United States Patent [19]

Yamashita et al.

[11] Patent Number: 4,906,176
[45] Date of Patent: Mar. 6, 1990

[54] HIGH TEMPERATURE STABLE CATALYST, PROCESS FOR PREPARING SAME, AND PROCESS FOR CONDUCTING CHEMICAL REACTION USING SAME

[75] Inventors: Hisao Yamashita; Akira Kato, both of Hitachi; Shigeo Uno, Toukai; Mamoru Mizumoto; Shinpei Matsuda, both of Hitachi, all of Japan

[73] Assignee: Hitachi, Ltd., Tokyo, Japan

[21] Appl. No.: 135,064

[22] Filed: Dec. 18, 1987

Related U.S. Application Data

[60] Division of Ser. No. 867,542, May 28, 1986, Pat. No. 4,738,946, which is a continuation of Ser. No. 627,104, Jul. 2, 1984, abandoned.

[30] Foreign Application Priority Data

Jul. 1, 1983 [JP] Japan ................................ 58-118207
Jul. 15, 1983 [JP] Japan ................................ 58-127947

[51] Int. Cl.$^4$ ................................................ F23D 3/40
[52] U.S. Cl. .......................................... 431/7; 502/303; 502/304; 502/355; 502/439; 502/527
[58] Field of Search ............... 431/2, 7; 502/303, 355, 502/304, 327, 439, 527

[56] References Cited

U.S. PATENT DOCUMENTS

| | | | |
|---|---|---|---|
| 3,714,071 | 1/1973 | Michalko | 502/355 |
| 3,867,312 | 2/1975 | Stephens | 423/213.5 |
| 3,899,444 | 12/1972 | Stephens | 423/213.5 |
| 3,956,188 | 5/1976 | Hindin et al. | 431/2 |
| 3,966,391 | 6/1976 | Hindin et al. | 423/213.5 |
| 3,993,572 | 11/1976 | Hindin et al. | 423/213.5 |
| 4,008,037 | 2/1977 | Hindin et al. | 431/2 |
| 4,021,185 | 5/1977 | Hindin et al. | 431/7 |
| 4,056,489 | 11/1977 | Hindin et al. | 502/257 |
| 4,061,594 | 12/1977 | Michel et al. | 502/302 |
| 4,170,573 | 10/1979 | Ernest et al. | 502/303 |
| 4,220,559 | 9/1980 | Polinski | 502/255 |
| 4,400,356 | 8/1983 | McVay et al. | 126/58 |
| 4,415,537 | 11/1983 | Vine et al. | 126/217 |
| 4,537,873 | 8/1985 | Kato et al. | 502/303 |
| 4,585,752 | 4/1986 | Ernest | 502/358 |
| 4,738,946 | 4/1988 | Yamashita et al. | 502/303 |
| 4,793,797 | 12/1988 | Kato et al. | 431/7 |

OTHER PUBLICATIONS

Dexpert-Chys et al, Optical and Structural Investigation of the Lanthanum $\beta$-Alumina Phase Doped with Europium, Journal of Solid State Chemistry, 19, 193–204 (1976).

Primary Examiner—Anthony McFarlane
Attorney, Agent, or Firm—Antonelli, Terry & Wands

[57] ABSTRACT

The disclosure is concerned with a high temperature stable catalyst comprising an alumina base support and a catalytically active component supported on the support. The support is featured by its specific composite oxide having a specific surface area of at least 10 m$^2$/g and a structural form of amorphous state or a phase resemble to lanthanoide $\beta$-alumina. The composite oxide can be converted to lanthanoide $\beta$-alumina when heated to an elevated temperature above 1000° C. within 2 hours. The composite oxide is substantially free from such ingredients as accelerate grain growth of alumina. The ingredients are for example Cr, Sr or Ce.

The present dislcosure is also concerned with a process for preparing the catalyst and a process for conducting chemical reactions such as steam reforming, desulfurization of heavy oil, cracking of hydrocarbons, etc. using the catalyst.

14 Claims, 3 Drawing Sheets

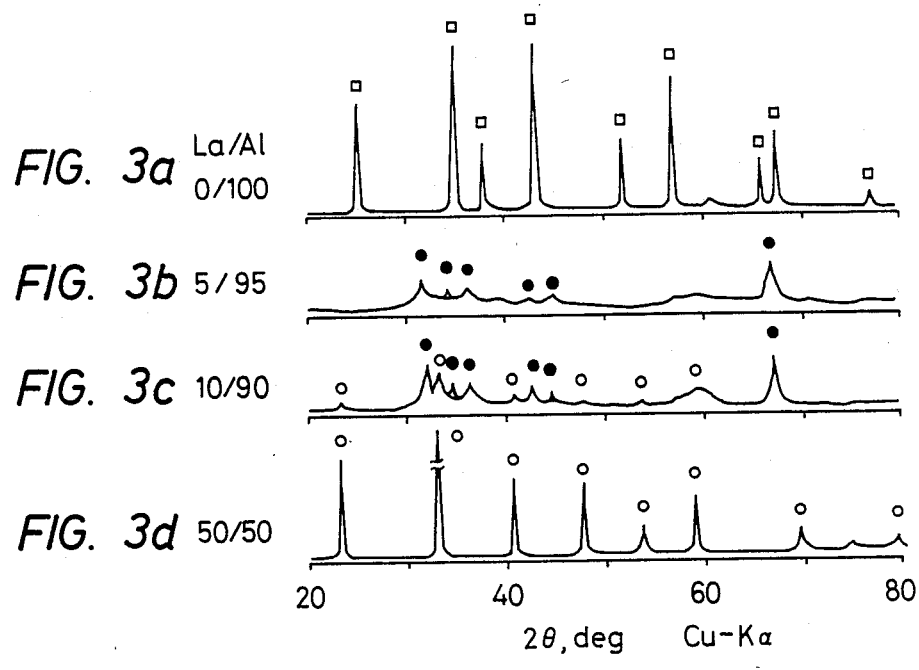
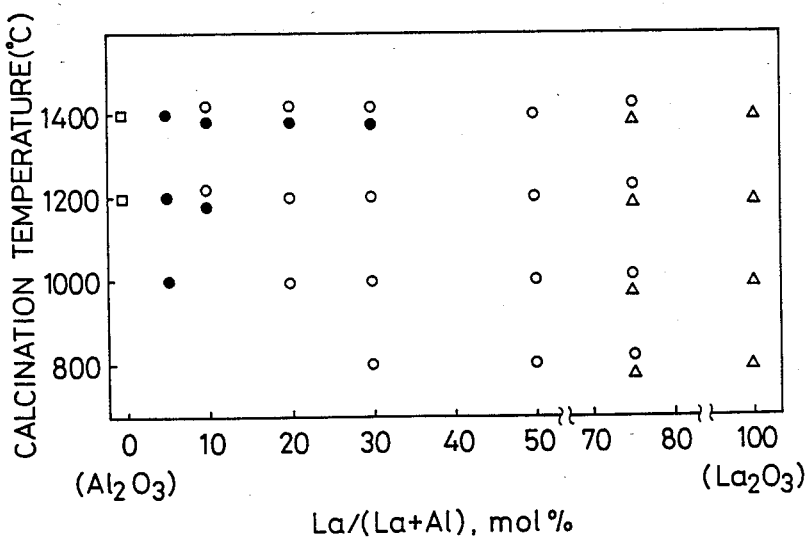

HIGH TEMPERATURE STABLE CATALYST, PROCESS FOR PREPARING SAME, AND PROCESS FOR CONDUCTING CHEMICAL REACTION USING SAME

This is a division of application Ser. No. 867,542, filed May 28, 1986, now U.S. Pat. No. 4,738,946, which is a continuation of application Ser. No. 627,104, filed July 2, 1984, now abandoned.

DETAILED DESCRIPTION OF THE INVENTION

Field of the Invention

The present invention relates to a high temperature stable catalyst, a process for preparing the same and a catalytic reaction process using the high temperature stable catalyst.

The catalyst used in the present invention is highly active over a very wide range of temperature and particularly stable even at a temperature of 800° C. or above.

BACKGROUND OF THE INVENTION

As reactions which are carried out in the presence of a catalyst at a high temperature, there have been known treatment of an organic solvent or deodorization by oxidiation, treatment of automobile exhaust gas, high-temperature steam reforming and high-temperature denitration. Recently, a catalytic combustion technique is employed in large-volume boilers, gas turbines and aircraft gas turbines.

In these treatment processes, a reaction temperature of at least 600° C. is employed and under some conditions, a temperature of as high as 1400° to 1500° C. is employed. Therefore, catalysts having a high thermal stability the activity of which is not seriously damaged at such a high temperature are demanded.

As high-temperature catalysts, there have been used those comprising a noble metal or a base metal supported on a carrier comprising alumina, silica or silica/alumina; or those comprising a noble metal component supported on a carrier comprising a ceramic material such as zirconia, aluminum titanate or silicon nitride coated with active alumina or the like.

However, these catalysts have defects that when they are heated to a temperature of generally above 800° C., the specific surface area thereof is reduced due to phase transition of the carrier or crystal growth and also the surface area is reduced due to coagulation of the active component to deteriorate the catalytic activity thereof remarkably. The catalysts made of the ceramic material have a defect that the catalytic component cannot be used effectively, since the heat resistance of the coating material is low.

There have been known catalysts wherein carrier materials are made of $Al_2O_3$: and lanthanoides as disclosed in the following U.S. Patents.

(1) U.S. Pat. No. 3,993,572 "Rare Earth and Platinum Group Metal Catalyst Composition"
(2) U.S. Pat. No. 3,966,391 "Method of Combustion using High Temperature Stable Catalysts"
(3) U.S. Pat. No. 3,956,188 "Compositions and Methods for High Temperature Stable Catalysts"
(4) U.S. Pat. No. 3,899,444 "Exhaust Gas Catalyst Support"
(5) U.S. Pat. No. 3,867,312 "Exhaust Gas Catalyst Support"
(6) U.S. Pat. No. 3,714,071 "Low Density Alumina Spheres of Improved Strength at High Temperature"
(7) U.S. Pat. No. 4,056,489 "Hih Temperature Stable Catalyst Composition and Method for its Preparation"
(8) U.S. Pat. No. 4,021,185 "Compositions and Methods for High Temperature Stable Catalyst"
(9) U.S. Pat. No. 4,220,559 "High Temperature-Stable Catalyst Composition"
(10) U.S. Pat. No. 4,061,594 "Alumina-based Bodies Obtained by Agglomeration which are resistant to Elevated Temperature"

Other prior arts include U.S. Pat. Nos. 3,978,004, 3,956,186, 3,931,050, 3,898,183, 3,894,140, 3,883,445, 3,880,775, 3,867,309, 3,819,536, 4,374,819, 4,369,130, 4,318,894, 4,233,180, 4,206,087, 4,177,163, 4,153,580, 4,170,573, and 4,054,642.

Among the prior art listed above, U.S. Pat. Nos. 3,966,391, 4,170,573 and 4,061,594 seem to be relevant to the present invention. The U.S. Pat. No. '391 discloses a process for producing a catalyst which comprises preparing a solution containing $La(NO_3)_3$, $CrO_3$ and $Sr(NO_3)_3$, adding $Al_2O_3$ powder in the solution, stirring the mixture to impregnate the $Al_2O_2$ powder with the solution, heating the mixture under stirring to evaporate the liquid, drying the mixture at 110° C., and calcining the dried mixture at 1200° C. for 2 hr. The catalysts obtained are used for combustion of carbonaceous fuel.

The U.S. Pat. No. '573 discloses a process for preparing a catalyst which comprises impregnating $Al_2O_3$ powder with an $La(NO_3)_3$ solution, drying the impregnated $Al_2O_3$ powder at 160° C. for 16 hrs, calcining the dried $Al_2O_3$ powder at 1250° C. for 1 hr, impregnating the calcined $Al_2O_3$ powder with a $Ce(NO_3)_3$ solution, drying the impregnated La-Ce-$Al_2O_3$ powder at 160° C. for 16 hrs, impregnating the La-Ce-$Al_2O_3$ powder with a $PtCl_4$ solution, and calcining the Pt-La-Ce-$Al_2O_3$ powder at 427° to 649° C.

The U.S. Pat. No. '594 discloses a process for producing a catalyst which comprises autoclaving $Al_2O_3$ at 600° C., calcining the precipitate at 500° C., impregnating the calcined with a $La(NO_3)_3$ solution, drying the impregnated $Al_2O_3$, impregnating the dried $La_2O_3$-$Al_2O_3$ with a solution of a platinum group element, and calcining the impregnated $La_2O_3$-$Al_2O_3$ at 1000° C. or 1200° C.

Journal of Solid State Chemistry 19, 193–204 (1976) discloses structural investigation of the lanthanum β-Alumina phase, the disclosure of which is not concerned with a catalyst.

SUMMARY OF THE INVENTION

An object of the present invention is to provide a catalytic reaction process using a heat-resistant catalyst. γ- or η-Alumina having a high specific surface area has been used frequently as a carrier or coating material. However, at a temperature of above 800° C., particularly above 900° C., the specific surface area is reduced due to the phase transition into α-alumina and increase of the crystal particle diameter and, consequently, the particles of the noble metal or base metal used as the catalytically active component are coagulated to deteriorate the catalytic activity.

After intensive investigations made for the purpose of overcoming the thermal unstability of alumina and also preventing the coagulation of the particles of the catalytic component supported on the carrier, the inventors have found that a catalyst comprising a catalytically active noble metal or base metal supported on a lanthanum β-alumina ($La_2O_3 \cdot 11-14Al_2O_3$), praseodymium β-alumina ($Pr_2O_3 \cdot 11-18Al_2O_3$), neodymium β-alumina ($Nd_2O_3 \cdot 11 \sim 14Al_2O_3$); (hereinafter referred to as L-β-alumina) carrier obtained by adding lanthanum to aluminum is quite effective.

The present invention provides a heat-resistant catalyst comprising a catalytically active component supported on a support containing a composite oxide of aluminum and lanthanum.

The composite oxide of aluminum and lanthanum is a mixture of lanthanum β-alumina and a precursor that is convertible to lanthanum β-alumina when heated to a temperature of 1000° C. for 2 hours, or the composite oxide consists substantially of the precursor.

The high temperature stable catalyst of the present invention comprises a support and a catalytically active component supported on said support, wherein at least the part of said support that predominantly supports said active component comprises a composite oxide of aluminium and at least one member selected from the group of lanthanum, neodymium, praseodymium and mixtures thereof, said composite oxide having a specific surface area of at least 10 $m^2/g$, where said composite oxide contains less than 1% by weight of chromium, strontium and cerium, and is a mixture of L-β-alumina and its precursor that is convertible to L-β-alumina when heated to an elevated temperature above 1000° C. within 10 hours or substantially the precursor.

BRIEF DESCRIPTION OF THE DRAWINGS

FIGS. 3a to 3d are X-ray diffraction patterns of $La_2O_3 - Al_2O_3$ with various La/Al ratio, wherein calcination was conducted at 1200° C. for 2 h. □ denotes α-$Al_2O_3$, ● La-β$Al_2O_3$ and ○ $LaAlO_3$.

FIG. 4 is a graph showing the relationship between formation of $La_2O_3 \cdot Al_2O_3$ compounds observed X-ray diffraction analysis. □ denotes α-$Al_2O_3$, ● La-β-$Al_2O_3$, ○ $LaAlO_3$ and △ $La_2O_3$.

DETAILED DESCRIPTION OF THE INVENTION

Figure 1:
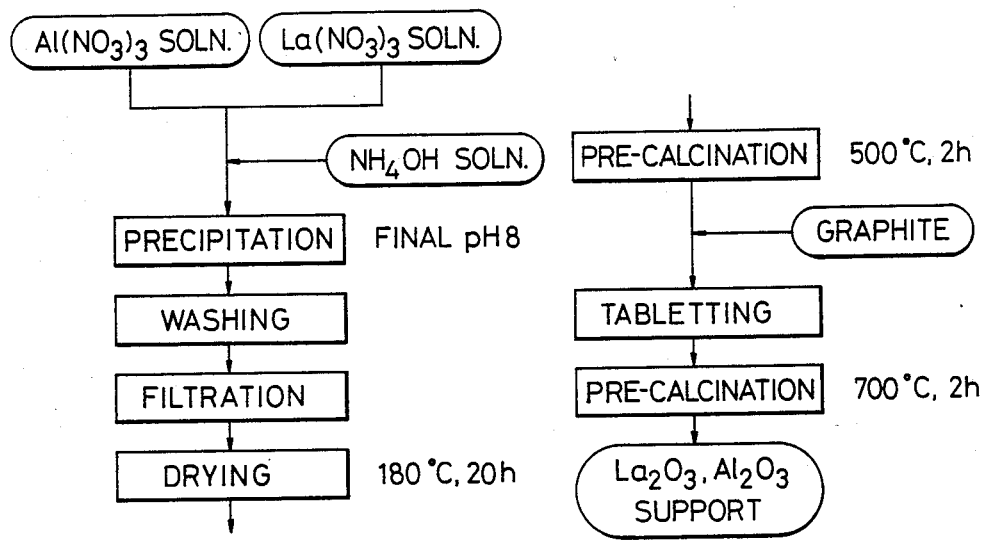
FIG. 1 is a flow chart showing preparation of $La_2O_3 \cdot Al_2O_3$ support.

The L-β-alumina is a compound represented by the formulae: $La_2O_3 \cdot 11-14Al_2O_3$, $Pr_2O_3 \cdot 11-14Al_2O_3$ or $Nd_2O_3 \cdot 11-14Al_2O_3$. These composite oxides are obtained by heat-treating hydroxides or oxides of Al and La, Nd and/or Pr or by calcining a mixture of starting compounds which yield the oxides by heat treatment at a temperature of 800° C. or higher.

Even when the catalyst comprising a catalytically active component supported on the support made of the composite oxides of aluminum and lanthanum, praseodymium and/or neodymium is used at a temperature of as high as 1000° C. or above, the catalytically active component is hardly coagulated by heat and its stable catalytic activity can be maintained, since the interaction between the composite oxide of aluminum and lanthanum, etc. and the catalytically active component is strong.

The composite oxide is a mixture of L-β-alumina and its precursor or the composite oxide is made of the precursor. The composite oxide mentioned above has a high heat resistance and a large specific surface area. Further, it has been made apparent from detailed X-ray diffraction and electron microscopic observation that this compound has an effect of retarding the phase transition from active alumina into - alumina and the crystal growth.

It has been made apparent from $N_2$ adsorption tests that the reduction of the specific surface area of the support comprising the composite oxide of aluminum and lanthanum (hereinafter the description is made with respect to La for simplicity) at a high temperature is only small. The dispersion state of palladium or platinum (catalytic component) supported on said composite oxide was examined by electron microscopy and carbon monoxide chemical adsorption method to reveal that the good dispersion state was maintained even after thecalcination at 1200° C.

The composite oxide of aluminum and lanthanum may be applied to a ceramic material to form a coating or the former may be mixed with the latter. For example, the composite oxide may be used in the form of a mixture with a heat-resistant oxide such as α-alumina, titania, zirconia, magnesia, cordierite, mullite or aluminum titanate Further, the composite oxide may be applied to a material other than the oxides, such as silicon carbide or silicon nitride, to form a coating or the former may be mixed with the latter. In forming the mixture, the amount of the composite oxide of aluminum and lanthanum is controlled preferably to at least 50% based on the total amount of the support. In case of preparation of the support by coating, a gel or solution of salts of Al and La, Pr and/or Nd which can be prepared by, for example, coprecipitation is coated on a ceramic or metallic support and the coating is dried and calcined to obtain the desired porous heat-resistant support surface.

The following facts have been confirmed by the present inventors.

(1) Lanthanum, praseodymium and neodymium have exhibited the similar effect on the stabilization of the support at elevated temperature. However, cerium which is one of rare earth metals gave adverse effect on the stabilization. Further other elements such as chromium, zirconium, strontium, calcium, sodium showed acceleration of sintering or grain growth of alumina when the $Al_2O_3$ support containing Cr, Sr, Ca, Na is calcined at 1200° C. or higher. This phenomena results in the reduction of the surface area of the support.

(2) The composite oxide should have a specific surface area of at least 10 $m^2/g$, and be in the form of an amorphous state, or a structure resembling to L-β- alumina or a precursor which can be converted to L-β-alumina when heated to 1400° C. for 2 hours. The composite oxide should be in the structural form other than α-, γ-, θ-, η-, κ-, χ-, ρ- or δ-form. The surface area of the composite oxide should preferably be 20 to 100 m²/g.

(3) The amounts of L-β-Al₂O₃ in the composite oxide are in the range of from about 15 to about 95% by weight. When the molar ratio of La₂O₃ to Al₂O₃ in the starting material (i.e. before calcination) is 1 to 99, the amount of L-β-Al₂O₃ is about 15% by weight. When the molar ratio of La₂O₃ to Al₂O₃ is 20 to 80, the amount of L-β-Al₂O₃ is about 95% by weight. is pb 20 to 80, the amount of L-βAl₂O₃ is about 95% by weight. Similarly, at the molar ratio of La₂O₃ to Al₂O₃ being 10 to 90, the amount is about 90% by weight, at the ratio of La₂O₃ to Al₂O₃ being 5 to 95, the amount is about 64% by weight, and at the molar ratio of La₂O₃ to Al₂O₃ being 2 to 98, the amount of L-β-Al₂O₃ is about 27% by weight.

The amount of the mixture of L-β-Al₂O₃ and its precursor or the precursor in the composite oxide should be predominant or at least 50% by weight.

L-β-Al₂O₃ has characteristic peaks at degrees of 18.9 ⑦, 20.1 ⑨, 32.3 ⑤, 34.0 ②, 36.2 ①, 39.4 ⑧, 40.9 ⑩, 42.8 ④, 45.1 ⑥, 58.0 ⑪ and 67.4 ③ in terms of Bragg angles (2θ) of X-ray diffract pattern. The circled numbers represent the order of the strengths of peaks. The composite oxide calcined at 1200° C. showed characteristic peaks at 18.9°, 20.1°, 32.3°, 34.0°, 36.2°, 42.8°, 45.1°, 58.0° and 67.4°; this fact means that the composite oxide contains L-β-Al₂O₃ (see FIGS. 3b to 3c).

Since the diffraction patterns shown in FIGS. 3b and 3c are somewhat broadened, compared to those of crystal forms (FIGS. 3a and 3d), the composite oxide comprises L-β-Al₂O₃ and the precursor which may be a form other than α-, γ-, θ-, η-, κ-, δ-, χ- or ρ-form, but the precursor should be amorphous. In FIGS. 3b and 3c there are marked by black dots peaks at 32.3°, 36.2°, 42.8°, 45.1° and 67.4°.

(4) When an alumina support of such as α-, γ-, θ-, δ-, η-, κ-, χ- or ρ-form is impregnated with a solution of lanthanum, praseodymium and/or neodymium salt and calcined at a temperature of 1000° to 1200° C. for 2 hours, an appreciable amount of L-β-alumina is not produced on or in the surface of the support.

The high temperature stable catalyst according to the invention may employ a support which is wholly made of the composite oxide.

The high temperature stable catalyst according to the invention can have the shape of a honeycomb structure.

The high temperature stable catalyst according to the invention may comprise the part for supporting the active component and a substrate for carrying the support.

The substrate can be made of a member selected from a metallic plate, metallic mesh, and foamed metal.

The high temperature stable catalyst according to the invention can have a surface of the support coated with the composite oxide on which said active component is supported.

A process which is preferentially employed for preparing a high temperature stable catalyst comprises effecting coprecipitation of an aluminum salt and a salt of lanthanium, praseodymium and or neodymium from an aqueous solution of the salts by adding an alkali to the solution;

separating the resulting precipitate;

shaping the precipitate; and heating to a temperature higher than 1000° C. the shaped precipitate to convert it into a composite oxide of aluminium and lanthanum, neodymium and/or praseodymium, whereby said composite oxide has a specific surface area of at least 10 m²/g, and a structural form other than α-, γ-, θ-, η-, κ-, χ-, ρ-and δ- forms is a precursor convertible to L-β-aIumina when heated to a temperature above 1000° C. within 2 hours or a mixture of L-β-alumina and the precursor.

Further, the catalyst support for the present invention may be prepared by homogeneously mixing fine powders of oxides or salts of aluminium and lanthanum, neodymium and/or praseodymium in the dry state or wet state, shaping the mixture, and calcining the mixture at a temperature of 800° C. or above, preferably at 1000° C. or above to produce the desired precursor or the mixture.

If the calcination temperature for preparing the support is lower than 800° C., the precursor can not be appreciably converted to L-β-alumina when heated to a temperature above 1000° C. within 2 hours.

The support of the invention can be prepared by the following manners:

(1) A starting material of the composite oxide, i.e. a homogeneous mixture of salts of Al and La, is preliminarily calcined at a temperature of, for example, 800° C. or below.

Then the resulting precursor of the composite oxide is calcined at a temperature of 900° C. or higher for a predetermined period of time so that the precursor is converted to a desired mixture of L-β-alumina and its precursor or the precursor that is convertible to L-β-alumina when heated to a temperature above 1000° C. within 10 hours.

(2) The starting material of the composite oxide is preliminarily calcined at a temperature of, for example, 800° C. or below. Then, the resulting precursor of the composite oxide is impregnated with a solution of a catalytically active component or is coated with the catalytically active component to support the component on the precursor of the composite oxide. The resulting product is then calcined at a temperature of 900° to 1500° C. for a predetermined period of time to convert the precursor to another form of composite oxide, i.e. a mixture of L-β-alumina and the precursor of L-β-alumina.

The calcination temperature for forming the desired composite oxide of Al and La is above 900° C., preferably 1000° C. If a calcination temperature is lower than 900° C., the desired composite oxide can not be obtained with a practical period of time.

The structural feature of the composite oxide of the present invention may be amorpous or a structure resembling L-β-alumina. The structure is dependent on the calcining conditions, particularly temperature and time periods. The higher the temperature for calcining, the higher the degree of conversion of the structure of the composite oxide to the L-β-alumina becomes.

When the precursor of the composite oxide is calcined at 1500° C. for 1 hour or longer, the crystal growth of the composite oxide is too much, resulting in reduction of the specific surface area.

Even when the calcining temperature is 900° C., the desired composite oxide may be obtained when the calcining is conducted at 900° C. for 100 hours or longer.

The calcining conditions are chosen from the practical point of view. Preferable calcining conditions are in the range of from 1000° C.×at least 1 hours to 1400° C.×0.5 hours or less. The pressure for calcinination does not have signification.

The most preferable calcining conditions are in the range of from 1100° C.×1 to 10 hours to 1300° C.×0.5 to 2 hours under a pressure of 100 kg/cm² or less.

A powder containing the composite oxide may be shaped into in various forms such as globules, cylinders, rings and honeycombs. A slurry of the powder containing the composite oxide may be applied to a metallic substrate such as metallic plate, mesh, foamed metal, or to an inorganic heat-resistant support such as ceramic material, for example, mullite, cordierite, α-alumina, zircon, aluminum titanate, silicon carbide or silicon nitride in various shapes to form a coating. The amount of the composite oxide to be supported on the inorganic heat-resistant support is at least 5%, preferably 5 to 30%, based on the total weight of the support.

The composite oxide of aluminum and lanthanum may be prepared by, for example, an ordinary precipitation method, deposition method, kneading method or impregnation method.

Among the methods mentioned above, a coprecipitation method is most suitable for producing a highly homogeneous complex oxide. Moreover, the coprecipitation method is most effective to produce L-$\beta$-alumina or its specific precursor.

The composite oxide may be prepared by coprecipitation or a method wherein alumina and/or alumina sol are mixed intimately with lanthanum oxide and/or lanthanum hydroxide and the resulting mixture is calcined; or a method wherein alumina is impregnated with a lanthanum salt solution and then calcined by heating.

It is preferred to coprecipitate an intimate mixture of aluminum and lanthanum by adding an alkali to an aqueous solution containing aluminum and lanthanum prior to the calcination, since the intended composite oxide of aluminum and lanthanum can be obtained even at a relatively low calcination temperature.

Starting materials for aluminum usable in the present invention include soluble salts such as nitrate, sulfate and chloride; organic salts such as alkoxides; hydroxide; and oxide thereof. Starting materials for lanthanum, neodymium and praseodymium usable in the present invention include soluble salts such as nitrate, chloride and oxalate; hydroxide; and oxide thereof.

A rare earth mixture containing lanthanum, neodymium and/or praseodymium but substantially free from cerium may also be used.

The catalytically active component is supported on the support finally in the form of the metal or its oxide.

The catalytically active component may be supported on the carrier by an ordinary method such as impregnation or kneading. Starting materials for the catalytically active components include inorganic salts and complex salts.

The catalyst of the present invention is usable for combustion reactions of fuels such as hydrogen, carbon monoxide, hydrocarbons or alcohols, deodorization, denitration reaction, high-temperature steam reforming reaction and cleaning of automobile exhaust gas.

When the catalyst of the present invention is used for the combustion reaction of at least one combustible component selected from the group consisting of hydrogen, carbon monoxide, alcohols and hydrocarbons, it is desirable to use a Group VIII element of the Periodic Table, manganese, chromium, zirconium, rare earth element, tin, zinc, copper, magnesium, barium, strontium or calcium as the catalytically active component. The fuels to be subjected to the combustion reaction include, for example, methane, ethane, propane, butane, kerosene, diesel oil, light oil, etc.. The reaction temperature which varies depending on the kind of the fuels ranges broadly from room temperature to 1500° C. In the combustion reaction, said gas is contacted with the catalyst in the presence of an oxygen-containing gas. When methane is used as the fuel, a reaction temperature in the range of 400° to 1500° C. is particularly preferred and a platinum group metal is used preferably as the catalytically active component.

When the catalyst of the present invention is used for cleaning an exhaust gas from an internal combustion engine of, for example, an automobile, there is used at least one catalytically active component selected from the group consisting of Group VIII elements of the Periodic Table, manganese, chromium, zirconium, rare earth elements, tin, zinc, copper, magnesium, barium, strontium and calcium and the exhaust gas and oxygen are contacted with the catalyst at a reaction temperature of 150° to 1500° C. It is particularly preferred to use a Group VIII metal of the Periodic Table as the catalytically active component.

By this treatment, carbon monoxide and hydrocarbons contained in the exhaust gas can be oxidized and nitrogen oxides can be converted into harmless nitrogen and water.

When the catalyst of the present invention is used for the steam reforming of hydrocarbons, at least one member selected from the group consisting of Group VIII elements of the Periodic Table, alkali metals and alkaline earth metals is used as the catalytically active component and the reaction is carried out in the temperature range of 400° to 1000° C. to form a gas comprising hydrogen and carbon monoxide. It is preferred to use the Group VIII elements of the Periodic Table, particularly nickel or a mixture of nickel and cobalt as the catalytically active component.

When the catalyst of the present invention is used for the reduction of nitrogen oxides contained in an exhaust gas from a boiler or a gas turbine, the reaction is carried out using ammonia as a reducing agent at a temperature of 400° to 1500° C. It is preferred to use at least one member selected from the group consisting of Group VIII elements of the Periodic Table, alkaline earth metals, titanium, zirconium, vanadium, rare earth elements, Groups Va and VIa elements of the Periodic Table, manganese, zinc, aluminum and tin as the catalytically active component(s).

They are supported on the carrier finally in the form of their oxides. Particularly preferred catalytically active component is at least one of tungsten, vanadium, titanium, tin, cerium, iron, nickel and/or cobalt.

When the catalyst of the present invention is used for the methanation, it is preferred to use at least one member selected from the group consisting of Group VIII elements of the Periodic Table, zinc, chromium, molybdenum, tin, vanadium and cerium as the catalytically active component and a carbon monoxide-containing gas and hydrogen are contacted with the catalyst at a temperature of 250° to 800° C. Preferred catalytically active component is a Group VIII metal of the Periodic Table, particularly nickel.

When the catalyst of the present invention is used for the dehydrogenation reaction of hydrocarbons, at least one catalytically active component selected from the group consisting of chromium, zinc, vanadium, copper, silver, iron, nickel and cobalt is used and the hydrocarbons are contacted with the catalyst at a temperature in the range of 300° to 1000° C. It is desirable to use at least one of copper and zinc as the catalytically active component.

PREPARATORY EXAMPLE

Preparation of $La_2O_3.Al_2O_3$ Supports

A procedure for preparation of $La_2O_3.Al_2O_3$ supports is shown in FIG. 1. A mixed solution of $La(NO_3)_3$ and $Al(NO_3)_3$ was neutralized by addition of an $NH_4OH$ solution and the precipitate was washed throughly and dried. After preliminary calcining at 500° C., the powder with 1 wt % graphite was tabletted into a columnar shape of 3 mm diameter and 3 mm height. A support consisting of $La_2O_3$ and $Al_2O_3$ was obtained by preliminary calcining the tablets at 700° C. for 2 hours. For comparisons a support consisting only of $Al_2O_3$ or $La_2O_3$ was also prepared by the same procedure. A mixed oxide consisting of 5 mol % $La_2O_3$ and 95 mol % $Al_2O_3$ is denoted as $La_2O_3.Al_2O_3$ (5/95) in the following part of this paper. To give an example, a BET surface area of 130 $m^2/g$ and porosity of 0.40 ml/g (measured by water pick-up) were obtained for $La_2O_3.Al_2O_3$ (5/95) support.

Preparation of Pd Catalyst

The support was impregnated in a $Pd(NO_3)_2$ solution, the Pd loading in the final catalyst being 1 wt %. The Pd catalysts supported on the $La_2O_3.Al_2O_3$ supports were preliminary calcined at 500° C. for 30 min. and subsequently at 1200° C. for 2 hours.

Experimental Apparatus

The activity of catalyst on the $CH_4$ oxidation was measured using a flow type reactor made of quartz with 18 mm inner diameter. A reaction gas mixture containing 0.1 vol % $CH_4$ in air was used to measure the activity under isothermal condition. A gas mixture containing 3 vol % $CH_4$ in air was used in a durability test which was performed at the inlet temperature of 500° C. and the catalyst bed temperature about 1150° C. (adiabatic flame temperature>1200° C.). The volume of catalyst was 8 ml and the gas flow rate 240 l/h (at STP), making a space velocity of 30,000 vol/vol/h.

The conversion of $CH_4$ oxidation was determined by measuring gaseous composition with a gas chromatograph. The crystallographic structure of the supports was investigated by an X-ray diffractometer (Rigaku Denki, RAD-γA), X-ray microanalyser and transmission electron micrograph (Hitachi HV-11DS). The valence state of Pd on the supports was examined by XPS (Kratos XSAM-800). Specific surface area was measured by the standard BET method, and the Pd metal surface area by the CO adsorption method.

Surface Area and Crystal Structure of $La_2O_3.Al_2O_3$

Figure 2:
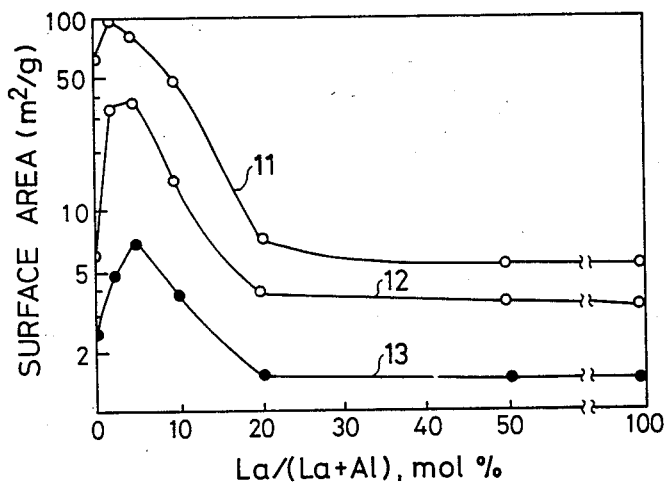
FIG. 2 is a graph showing the relationship between a surface area of $La_2O_3 \cdot Al_2O_3$ with various La/Al ratio calcined at 1000°, 1200°, 1400° C., wherein -○- denotes 1000° C., -◐- 1200° C., and -●- 1400° C.

The $La_2O_3.Al_2O_3$ supports with La content of 0, 2, 5, 10, 20, 50, 75, and 100 mol % were prepared and preliminary calcined at 700° C. The supports were treated in air at 1000° (curve 11), 1200° (curve 12), and 1400° C. (curve 13) for 2 hours. Changes of specific surface area are shown in FIG. 2. It is clearly shown that the surface area has a maximum between 2 and 5 mol % La. For the supports calcined at 1200° C., the surface area was 33 and 37 $m^2/g$ for $La_2O_3.Al_2O_3$ (2/98) and (5/95), respectively, whereas the surface area of Al O was 5.6 $m^2/g$. The surface area decreased gradually as the La content increased from 10 to 100 mol %. Thus, it has been found that the addition of only small amounts of $La_2O_3$ into $Al_2O_3$ markedly increases the thermal stability.

The crystal structure of the $La_2O_3.Al_2O_3$ supports was examined by X-ray diffraction analysis. FIGS. 3a to 3d show a few diffraction patterns obtained for the supports calcined at 1200° C. for 2 hrs. Peaks ascribed to $\alpha$-$Al_2O_3$ are observed in the $Al_2O_3$ support, 4 peaks ascribed to lanthanum-$\beta$-$Al_2O_3$ ($La_2O_3$-11$Al_2O_3$) in the $La_2O_3$. $Al_2O_3$ (5/95), and LaAlO in the $La_2O_3.Al_2O_3$ (50/50). It is seen that the peaks assigned to lanthanum-$\beta$-$Al_2O_3$ are rather weak and broad, indicating that crystal growth has proceeded only to a small extent. Therefore, the composite oxide obtained is considered as a precursor of lanthanum-$\beta$-alumina or a substance resembling to lanthanum-$\beta$-alumina.

When the calcining is conducted at 1000° C. for 2 hours, the resulting composite oxide showed no appreciable peaks like an amorphous structure. This is considered as a precursor of lanthanum-$\beta$-alumina. The above mentioned precursors could be converted to lanthanum-$\beta$-alumina by heating at 1400° C. for 2 hours. Lanthanum aluminate ($LaAlO_3$) which has a perovskite structure gives sharp peaks. In the $La_2O_3.Al_2O_3$ (10/90) the formation of both lanthanum-$\beta$-$Al_2O_3$ and $LaAlO_3$ is observed.

The formation of various $La_2O_3.Al_2O_3$ compounds observed by X-ray diffraction analysis between 800° and 1400° C. is summarized in FIG. 4. Lanthanum-$\beta$-$Al_2O_3$ or a product resembling to it is observed in the supports containing 2-30 mol % La, when calcined at 1400° C. $LaAlO_3$ is readily formed at the lower temperature. It is mentioned that the $Al_2O_3$ support calcined at 1200° C. gives very sharp peaks from $\alpha$-$Al_2O_3$, while the $La_2O_3.Al_2O_3$ (2/98) gives very weak peaks from $\theta$ and $\kappa$-$Al_2O_3$. The results indicate that the incorporation of small amounts of $La_2O_3$ into $Al_2O_3$ greatly retards the formation and the crystal growth of $\alpha$-$Al_2O_3$.

It is reported that La-$\beta$-$Al_2O_3$ is formed via $LaAlO_3$ at the temperature higher than 1400° C. by firing a $La_2O_3.Al_2O_3$ (8.3/91.7) mixture for 24 hrs "R. C. Ropp and B. Carroll, J. Am. Cer. Soc. 63, 416 (1980)". The formation of La-$\beta$-$Al_2O_3$ at the lower temperature, i.e. 1000° C. for 2 hours, in the present invention may result from the difference in the preparation method, i.e., the coprecipitation in the present invention and the mixing of two oxides. The coprecipitation method will give a better mixing of the two oxides.

Observation of the $La_2O_3$ $Al_2O_3$ supports by TEM was performed to investigate the particle size. Two typical electron micrographs were obtained as to (A) $Al_2O_3$ only, and (B) $La_2O_3.Al_2O_3$ (5/95). It has been found that $\alpha$-$Al_2O_3$ has grown up to a particle size of 500-1500 A, whereas the $La_2O_3.Al_2O_3$ has a particle size of 100-300 A. The $La_2O_3$ $Al_2O_3$ (50/50), i.e. $LaAlO_3$, showed a crystal growth to about 1000 A. It is reported in the literature "H. Schaper, et al, Applied Catalysis 7, 211 (1983)" that $La_2O_3$ decreases the sintering of $\gamma$-$Al_2O_3$ by the formation of $LaAlO_3$ at the surface layer. The present investigation, however, shows that the retardation of the sintering may be caused by the formation of lanthanum-$\beta$-$Al_2O_3$, not by $LaAlO_3$. The discrepancy may be attributed to difference of the preparation method, i.e. $\gamma$-$Al_2O_3$ tablets were impregnated in a La(-

$NO_3)_3$ solution in the literature. Since the concentration of $La_2O_3$ would be high at the surface layer in the impregnation method, the formation of $LaAlO_3$ is quite possible.

Activity of Pd-$La_2O_3$.$Al_2O_3$ Catalysts

Figure 5:
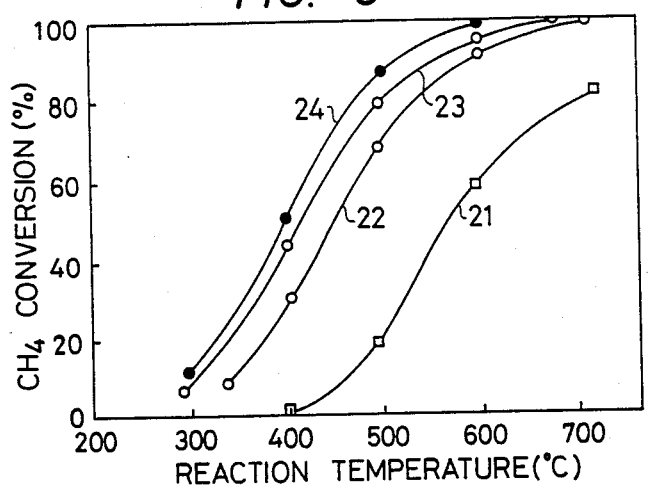
FIG. 5 is a graph showing activity of Pd-catalyst supported on $La_2O_3 \cdot Al_2O_3$ for $CH_4$ oxidation, wherein a gas mixture consisted of $CH_4$ 0.1% in air, and the catalyst was calcined at 1200° C. -□- denoted α-$Al_2O_3$, -●- La/Al=5/95, -◐- La/Al=10/90 and -○- Lq/Al=50/50.

Activities of the Pd catalysts on the oxidation of $CH_4$ were measured in a temperature range of 250° and 700° C. using a gas mixture containing 0.1% $CH_4$ in air. Under these conditions the reaction is carried out essentially isothermally. FIG. 5 shows the activity of the Pd catalysts supported on $La_2O_3$.$Al_2O_3$ with various La/Al ratios. The highest activity was obtained in the Pd-$La_2O_3$.$Al_2O_3$ (5/95) as shown by curve 24, while the Pd-$Al_2O_3$ showed a poor activity. The activity of Pd-$La_2O_3$.$Al_2O_3$ (2/98) shown by curve 24 was nearly equal to that of (10/90) shown by curve 23. It is noted that the Pd-$La_2O_3$.$Al_2O_3$ (50/50) shown by curve 22 showed a considerably high activity despite its low surface area of the support (see FIG. 2).

Figure 6:
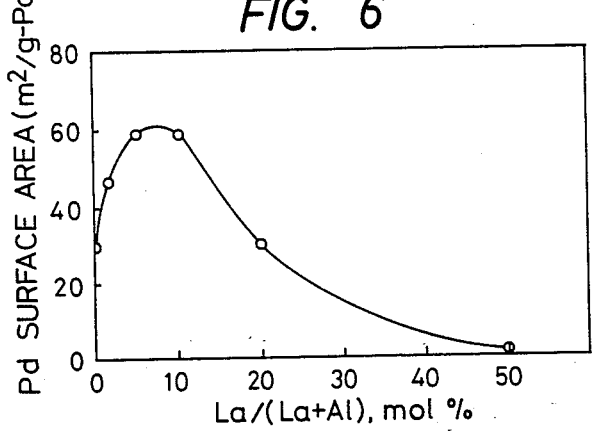
FIG. 6 is a graph showing the Pd surface area supported on $La_2O_3 \cdot Al_2O_3$.

A measurement of the Pd metal surface area was performed using the CO adsorption method in order to investigate the dispersion of Pd on the supports. The CO uptake at 200° C. was measured after treating catalysts in He stream at 250° C. FIG. 6 shows the Pd surface area of the catalysts as a function of La content. It is seen that the Pd surface area increases up to La content of 5-10 mol %, and then decreases to almost zero at 50 mol %.

Observation of the Pd catalysts by TEM was carried out to investigate Pd particle size on the supports. We obtained two electron micrographs, (A) Pd-$Al_2O_3$ calcined at 1000° C., and (B) Pd-$La_2O_3$.$Al_2O_3$ (5/95) calcined at 1200° C. Since the Pd particles were not always clearly identified on the micrographs, XMA was used to identify the locations of Pd particles. It was seen that the size of Pd particles is about 1500-2000 A on $Al_2O_3$, and 300-800 A on $La_2O_3$.$Al_2O_3$ (5/95). It may be said that Pd particles coagulate and sinter, as the crystal growth of the supporting $Al_2O_3$ proceeds. This is so called an "earthquake" effect.

Durability of Pd Catalyst Supported on La-$\beta$-$Al_2O_3$

Figure 7:
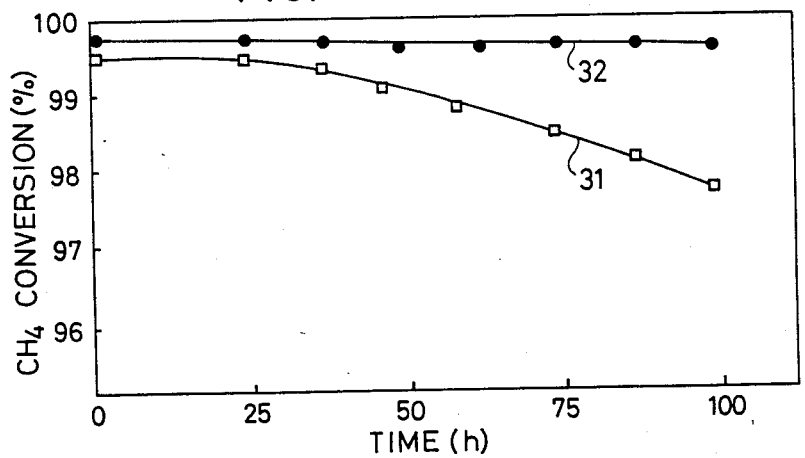
FIG. 7 is a graph showing durability of the Pd-catalyst supported on $Al_2O_3$ and $La_2O_3 \cdot Al_2O_3$ for $CH_4$ oxidation, wherein a gas mixture consisted of $CH_4$ 3% in air. The inlet temperature was 500° C. □ denotes α-$Al_2O_3$ calcined at 1000° C. and ○ La/Al=5/95 calcined at 1200° C.

Durability of the Pd combustion catalysts was treated using a gas mixture containing 3 vol % $CH_4$ at the inlet temperature of 500° C. and the catalyst bed temperature of about 1150° C. after $CH_4$ combustion. The test was carried out for 100 hours in the presence of two catalysts in parallel, one with Pd-$La_2O_3$.$Al_2O_3$ (5/95) and the other with Pd-$Al_2O_3$. The latter catalyst was calcined at 1000° C. instead of 1200° C., because the catalyst calcined at 1200° C. did not ignite the gas mixture at the inlet temperature of 500° C. .The result is shown in FIG. 7. The $CH_4$ conversion was maintained above 99.5% for the Pd-$La_2O_3$. $Al_2O_3$ (5/95) shown by curve 32, while it decreased from 99.5 to lower than 98% for the Pd-$Al_2O_3$ as shown by curve 31.

TABLE 1

|  | Pd—$Al_2O_3$ | | Pd—$La_2O_3$.$Al_2O_3$(5/95) | |
| --- | --- | --- | --- | --- |
|  | Fresh | After 100 h | Fresh | After 100 h |
| BET surface area ($m^2$/g) | 62 | 5.6 | 36 | 23.5 |
| Pd surface area ($m^2$/g-Pd) | 42 | 13.6 | 58.5 | 37 |

After the durability test the catalysts were examined by several methods. The BET surface area and the Pd metal surface area are summarized in Table 1. A drastic decrease in the surface areas is observed for Pd-$Al_2O_3$, and the change is relatively small for Pd-$La_2O_3$.$Al_2O_3$ (5/95). The activity of the two catalysts after the durability test was measured in a temperature range of 300° and 700° C. using the gas mixture containing 0.1 vol % $CH_4$ under isothermal condition. It was found that the rate constant was reduced by 15-20% relative to the initial value for the Pd-$La_2O_3$.$Al_2O_3$ (5/95) and 50-80% for the Pd-$Al_2O_3$. The TEM observation showed the existence of Pd particles as large as 3000-5000 A in the Pd-$Al_2O_3$ after the test.

The following examples will further illustrate the present invention, which by no means limit the scope of the protection of the present invention.

EXAMPLE 1

375.1 g of aluminum nitrate and 228 g of lanthanum nitrate were dissolved in 1 l of distilled water (Al/La atomic ratio: 95/5). 3N aqueous ammonia was added dropwise to the solution under stirring to neutralize the same to pH 7.5. The resulting coprecipitate of aluminum salt and lanthanum salt was washed thoroughly with water, dried, pulverized and calcined at 1000° C. for 5 h. The resulting powder was shaped into cylinders having 3 mm diameter and 3 mm length by means of a press molding machine.

Separately, a comparative support comprising only alumina was prepared in the same manner as above except that no lanthanum nitrate was used.

Each of the two carriers obtained as above was impregnated with 1 wt. % (as palladium) of a palladium nitrate solution, dried at 120° C. for about 5 h and then calcined at 1200° C. for 3 h to obtain catalysts of Example 1 and Comparative Example 1. The effects of them in the methane combustion reaction were examined. A continuous test was carried out for 1000 hours while a gas of the following composition was introduced at a space velocity of 25,000 $h^{-1}$.

Gas composition:

| methane | 3% |
| --- | --- |
| air | the balance |

In this experiment, the reaction gas was preheate 500° C. When the methane conversion has reached 90% or higher, the temperature of the catalyst bed is elevated to about 1200° C. The durability of the catalyst at high temperature can be evaluated from this fact. The results of the experiment are shown in Table 2.

It is apparent from Table 2 that the catalyst obtained in Example 1 is suitable for use in the catalytic combustion reaction at high temperature.

TABLE 2

| Catalyst | Methane conversion (%) Test time (h) | | | |
| --- | --- | --- | --- | --- |
|  | 1 | 50 | 100 | 1000 |
| Catalyst of Example 1 | >99.9 | >99.9 | >99.9 | >99.5 |
| Catalyst of Comparative Example 1 | 99.5 | 99.4 | 97.5 | 96 |

After the experiment for examining the activities of the catalysts of Example 1 and Comparative Example 1 effected for 100 h, surface areas of them were about 13.6 $m^2$/g and 5.6 $m^2$/g, respectively. The surface areas of palladium dispersed on the carrier were 37 $m^2$/g-Pd and 20 m²/g-Pd, respectively. Thus, it will be understood that as compared with the catalyst of Comparative Example 1, the catalyst of Example 1 had a larger specific surface area and more excellent Pd dispersion states so that the latter is an excellent heatresistant catalyst.

EXAMPLE 2

3750 g of aluminum nitrate and 480 g of lanthanum nitrate were dissolved in 10 l of distilled water. Then, the same procedure as in Example 1 was repeated to obtain a powder calcined at 1100° C. for 3 hours. 2.5 l of distilled water was added to 1 kg of the powder and the mixture was finely divided by means of an oscillating mill until an average particle diameter of the powder had been reduced to about 1 μm to obtain an impregnation liquid in the form of a slurry. A honeycomb structure (90 mm diameter and 75 mm length) made of a commercially available cordierite base material was immersed in the impregnation liquid and then taken out of the liquid. Compressed air was blown against the honeycomb structure to remove excessive liquid therefrom. After drying at 120° C., it was heat-treated at 500° C. for 1 h. This procedure was repeated and finally it was calcined at 1000° C. for 2 h. The thus treated honeycomb structure had 18.7 wt. % of a composite oxide layer. The specific surface area of the surface layer was 13.5 m²/g. The honeycomb structure was then immersed in an aqueous mixture of chloroplatinic acid and rhodium chloride, dried at 120° C. and reduced in hydrogen stream at 600° C. The catalyst contained 1.5 wt. % of platinum and 0.4 wt. % of rhodium.

The thus obtained catalyst was used for oxidation of an automobile exhaust gas. The catalyst was used as a catalytic converter for an ordinary automobile engine (1.8 l class). After 10,000 km travelling test, the results were 1.0 g/km of CO and 0.19 g/km of HC (in 10-mode). It is understood from these results that the heat-resistant catalyst of the present invention can be used for the treatment of an exhaust gas from an internal combustion engine to exhibit its effects stably in the high-temperature reaction.

EXAMPLE 3

In this example, the heat-resistant catalyst of the present invention was used in a high-temperature steam reforming reaction of hydrocarbons.

100 g of the support of the present invention obtained in Example 1 was impregnated with an aqueous nickel nitrate solution, dryed at 120° C. and calcined at 900° C. for 2 h. The catalyst thus obtained contained 15 wt. % (as NiO) of nickel.

The catalyst thus obtained was charged in a reaction tube and reduced in $H_2$ stream at 600° C. for 2 h. Then, a steam reforming reaction of n-butane was carried out while the inlet and outlet temperatures of the catalyst bed were maintained at 580° to 600° C. and 850° to 900° C., respectively, under a pressure of 15 kg/cm². The molar ratio of steam to carbon was 3.0 and space velocity was 3000 $h^{-1}$. After the continuous test effected for 100 h, n-butane conversion was maintained above 99.9%. After completion of the reaction, carbon deposit was hardly recognized on the catalyst bed. The gaseous reaction product comprised $H_2$, CO, $CO_2$ and $CH_4$. The ratio of these components was almost equal to that of an equilibrium composition obtained at the above-mentioned temperature of the catalyst bed outlet.

It is apparent from the results of this example that the heat-resistant catalyst of the present invention exhibits excellent effects also in the high-temperature steam reforming reactor.

EXAMPLE 4

In this example, the heat-resistant catalyst of the present invention was used in a high-temperature denitration reaction.

50 g of a powder of the composite oxide (not shaped) prepared in the same manner as in Example 1 was kneaded thoroughly with 500 g (150 g as $TiO_2$) of a metatitanic acid slurry by means of a kneader. The mixture was dried at 150° C. pulverized and preliminarily calcined at 400° C. for 4 h. The specific surface area of the support was 80 m²/g. The resulting powder was shaped into columnar moldings having 3 mm diameter and 3 mm thickness by means of a press molding machine. The moldings were then immersed in an aqueous hydrogen peroxide solution containing ammonium tungstate. After calcining them at 600° C. for 2 h, a catalyst containing 5 wt. % of tungsten oxide was obtained.

A gas having the following composition was treated at a reaction temperature of 600° C. and at a space velocity of 5000$h^{-1}$ for 100 h.

| Composition of reaction gas: | |
|---|---|
| $NO_x$ | 200 ppm |
| $NH_3$ | 200 ppm |
| $O_2$ | 3% |
| $H_2O$ | 10% |
| $N_2$ | the balance |

The $NO_x$ removal was 94.8% in the initial stage and 94.4% after 100 h. It is apparent from the above-mentioned results that the catalyst of the present invention exhibits excellent effects also in the high-temperature denitration reaction.

EXAMPLE 5

In this example, the catalyst of the present invention was sed in a methanization reaction of CO.

Each of the two supports obtained in Example 1 was impregnated with nickel nitrate, calcined at 500° C., then impregnated with ruthenium chloride and calcined at 1000° C. for 2 hours to obtain a catalyst. This catalyst contained 30% of NiO and 3% of Ru. The catalyst was charged in a reaction tube. A gas comprising 5% of CO, 17% of $H_2$ and the balance of $N_2$ was introduced therein at a space velocity of 100,000 $h^{-1}$. The methanation reaction was carried out at 350° C. The conversion of CO by the methanation reaction in this example was 15-folds of that obtained by using the catalyst of Comparative Example 1. It will be understood from these results that the catalyst of the present invention is quite effective not only for the high-temperature reactions but also for the relatively low-temperature reaction.

EXAMPLE 6

In this example, the effects of the catalyst in a dehydrogenation reaction of methanol were examined.

Each of the two carriers obtained in Example 1 was impregnated with a solution of copper nitrate or zinc nitrate. They were dried and then calcined at 1000° C. for 2 hours. The Cu and Zn contents of the carriers were 20 wt. % and 10 wt. %, respectively. The resulting carriers were each charged in a reaction tube and the temperature was elevated to 800° C. Methanol was introduced therein to effect the dehydrogenation reaction and to obtain formalin. Methanol conversion was at least 98% and formaldehyde selectivity was 5-folds of that obtained in a conventional process.

EXAMPLE 7

500 g of aluminum nitrate and 30.7 g of neodymium nitrate were dissolved in 5 l of distilled water. To the solution was added 3N aqueous ammonia under stirring to adjust a pH value thereof to 8 so as to effect coprecipitation.

The resulting precipitate was recovered by decantation and rinsed with distilled water, and then the precipitate was filtered. The precipitate obtained was dried at 150° C. for one day. The dried precipitate was crushed and pre-calcined at 500° C. for 2 hours; 0.5% by weight of graphite powder was added to the crushed calcining.

The powder mixture was shaped into a column of 3 mm diameter and of 3 mm length by means of a press molding machine.

The composition of the molding was 5 mol % of $Nd_2O_3$ and 95 mol % of $Al_2O_3$. The molding was then calcined at 1200° C. for 2 hours. The resulting support A had a specific surface area and a structure shown in Table 3.

EXAMPLE 8

Various supports having different molar ratios of $Al_2O_3$ and $Nd_2O_3$ were prepared in the same manner as in Example 7. The specific surface areas and structures of the composite oxides obtained are shown in Table 3 wherein support B has a composition of 2 mol % of $Nd_2O_3$-98 mol % of $Al_2O_3$; support C 10 mol % of $Nd_2O_3$-90 mol % of $Al_2O_3$ and support D 20 mol % of $Nd_2O_3$-80 mol % of $Al_2O_3$.

TABLE 3

| Support | Surface Area ($m^2/g$) | Structural form |
|---|---|---|
| A | 23.4 | Mixture of Nd-$\beta$-$Al_2O_3$ and the precursor |
| B | 21.5 | Mixed phase of Nd-$\beta$-$Al_2O_3$, the precursor and $\alpha$-$Al_2O_3$ |
| C | 19.3 | Mixed phase of Nd-$\beta$-$Al_2O_3$, the precursor and $\alpha$-$Al_2O_3$ |
| D | 14.2 | Mixed phase of Nd-$\beta$-$Al_2O_3$, the precursor and $\alpha$-$Al_2O_3$ |

EXAMPLE 9

500 g of aluminum nitrate and 30.5 g of praseodymium were dissolved in distilled water. Supports having compositions shown in Table 4 were prepared in the same manner as in Example 7. The surface areas and structural forms of the resulting supports were examined and are shown in Table 4, wherein support E has a composition of 2 mol % of $Pr_2O_3$ and 98 mol % of $Al_2O_3$; support F 5 mol % of $Pr_2O_3$ and 95 mol % of $Al_2O_3$; support G 10 mol % of $Pr_2O_3$ and 90 mol % of $Al_2O_3$; and support H 20 mol % of $Pr_2O_3$ and 80 mol % of $Al_2O_3$.

TABLE 4

| Support | Surface Area ($m_2/g$) | Structural form |
|---|---|---|
| E | 20.1 | Pr-$\beta$-$Al_2O_3$ |
| F | 22.9 | Mixed phase of Pr-$\beta$-$Al_2O_3$, the precursor and $\alpha$-$Al_2O_3$ |
| G | 17.5 | Mixed phase of Pr-$\beta$-$Al_2O_3$, the precursor and $\alpha$-$Al_2O_3$ |
| H | 13.0 | Mixed phase of Pr-$\beta$-$Al_2O_3$, the precursor and $\alpha$-$Al_2O_3$ |

EXAMPLE 10

500 g of aluminum nitrate, 18.6 g of neodymium nitrate and 18.5 g of praseodymium nitrate were dissolved in distilled water.

A support was prepared in the same manner as in Example 7. The support has a composition of 3 mol % of $Nd_2O_3$, 3 mol % of $Pr_2O_3$ and 94 mol % of $Al_2O_3$; a surface area of 23.0 $m^2/g$; and a structural form of a mixed phase of a phase resemble to Nd-$\beta$-alumina and Pr-$\beta$-alumina and $\alpha$-$Al_2O_3$.

EXAMPLE 11

500 g of alumina sol (alumina content: 9.8wt %) and 12.3 g of neodymium carbonate were kneaded with a kneader for 2 hours; then, the mixture was dried at 150° C. for one day.

The dried mixture was crushed to under 60 mesh; the resulting powder was pre-calcined at 500° C. for 2 h, mixed with 0.5% by weight of graphite powder, and was molded into pellets each having a diameter of 3 mm and a length of 3 mm.

The composition of the pellets was 4 mol % of $Nd_2O_3$ and 96 mol % of $Al_2O_3$. The pellets were calcined at 1000° C. 2 hours or 1200° C. for 2 hours. The resulting supports calcined at 1000° C. had a specific surface area of 96.5 $m^2/g$ and the supports calcined at 1200° C. had a specific surface area of 21.6 $m^2/g$.

Pd-Catalysts prepared in the same manner as in Example 1 using the supports obtained in Examples 7–10 exhibited good durability at temperatures as high as 800° to 1400° C.

Since the catalysts of the present invention have high specific surface areas, they can be used for chemical reactions at relatively low temperatures, as well as at high temperatures.

EXAMPLE 11

The support prepared in Example 1 was impregnated with a solution of ammonium molybdate and nickel nitrate, and was dried. Thereafter, the impregnated support was calcined at 500° C. for 5 hours. The composition of the catalyst obtained was 15% by weight of $MoO_3$ and 5% by weight of NiO, and the balance being the support.

40 ml catalyst was filled in a reactor having an inner diameter of 15 mm. Hydrogen gas was flown in the reactor at a rate of about 1 l/min. at 450° C. for 5 hours to reduce the catalyst.

Then, hydrogen gas was supplied to the reactor at a rate of 300 ml/min and n-hexane containing 100 ppm of thiophene was supplied at a rate of 100 ml/h to effect desulfurization reaction by hydrogenation. The content of sulfur in the effluent gas was determined by gas chromatograph. Even after the 100 hours test, the sulfur content was less than 0.1 ppm.

EXAMPLE 12

The support prepared in Example 1 was impregnated with a solution of chloroplatinic acid and was dried. The impregnated support was calcined at 900° C. for 2 hours. The content of platinum of the catalyst was 1% by weight.

5 cc of the catalyst was filled in a reactor to which air containing 100 ppm of methylethyl ketone, toluene and formaldehyde was supplied. The catalytic reaction was conducted at 500° C. The content of the odorous compounds in the effluent gas was only 0.4 ppm of methylethyl ketone, 0.3 ppm of toluene and 0.8 ppm of formaldehyde.

EXAMPLE 13

The powdered support prepared in Example 1 was thoroughly mixed with a slurry of β-stannic acid and the mixture was dried. The mixture was calcined at 500° C. for 3 hours. 1 g of the catalyst was added to 20 g of heavy oil. The oil was charged in an autoclave and subjected to a reaction at 400° C. under a pressure of 100 kg/cm$^2$ in the stream of hydrogen gas for 30 min. After the reaction, the product was subjected to distillation under a reduced pressure. The composition of the product was as follows:

| Boiling point (°C.) | Composition (% by weight) |
|---|---|
| ~ 200 | 9 |
| 200 ~ 350 | 39 |
| 350 ~ 550 | 37 |
| residue | 15 |

EXAMPLE 14

The support prepared in Example 1 was impregnated with a solution of copper chlorate and dried. The support was calcined at 500° C. for 2 hours. The composition of the catalyst was 20% by weight of Cu$_2$O and the balance being 80% by weight of the support.

An oxidation reaction of propylene was conducted using 20 ml of the catalyst. The reactive gas used was 25% by volume of C$_3$H$_6$, 10% by volume of O$_2$ and the balance being N$_2$. The reaction temperature was 450° C. The analysis of the product gas showed that the conversion rate of C$_3$H$_6$ to acrolein was 98% and the selection ratio to acrolein was 88%.

EXAMPLE 15

The support prepared in Example 1 was impregnated with a solution of cobalt nitrate and iron nitrate (III). The resulting impregnate was dried and calcined at 800° C. for 5 hours. The composition of the catalyst was 12% by weight of CoO, 8% by weight of Fe$_2$O$_3$ and the balance being the support.

40 ml of the catalyst was contacted with gas consisting of 40% by volume of CO and 60% by volume of H$_2$ at 300° C. under a pressure of 50 kg/cm$^2$. The conversion rate of [CO+H$_2$] to organic compounds was 88%. The selection ratios of the gas were 48% for C$_1$~C$_5$, 21% for gasoline 12% for oxygen-containing compounds, and 29% for heavy oil.

EXAMPLE 16

The support prepared in Example 1 was impregnated with copper nitrate, and zinc nitrate. The support was dried and calcined at 500° C. for 2 hours. The catalyst was contacted with a gas consisting of 75% by volume of H$_2$ and 25% by volume of CO at a temperature of 300° C. under a pressure of 100 kg/cm$^2$. The analysis of the product gas showed that the conversion rate of [Hz+CO] to methanol was 90% and the selection ratio for methanol was 92%.

EXAMPLE 17

The support prepared in Example 1 was impregnated with nickel nitrate and dried. The support was calcined at 500° C. for 2 hours to obtain a catalyst having a composition of 15% by weight of NiO and the balance being the support.

The catalyst was contacted with n-butane at 100° C. so as to effect isomerization reaction to iso-butane. The conversion rate of n-butane to iso-butane was 69%.

EXAMPLE 18

The support prepared in Example 1 was impregnated with cobalt nitrate and dried. The support was then calcined at 600° C. for 2 hours. The catalyst was used for cracking of heavy oil at 450° C. to produce a product containing about 40% by weight of gasoline distillate without deposition of carbon on the catalyst.

EXAMPLE 19

The support prepared in Example 1 was impregnated with a solution of iron chloride, potassium chloride and copper chloride and dried.

The catalyst was calcined at 700° C. for 2 hours to have a composition of 20% by weight of Fe$_3$O$_4$, 2% by weight of K$_2$O, 2% by weight of CuO, and the balance being the support.

The catalyst was then contacted with a gas consisting of 75% by volume of H$_2$ and 25% by volume of N$_2$ at 550° C. under a pressure of 250 kg/cm$^2$. The conversion rate of [Hz+N$_2$] to NH$_3$ was 95%.

What we claim is:

1. A process for conducting a catalytic oxidation reaction, which comprises contacting fluid fuel and an oxidant with a catalyst comprising a support and a catalytically active component supported on aid support, wherein at least the part of said support that predominantly supports said active component consists essentially of a composite oxide of aluminum and at least one member selected from the group consisting of lanthanum, neodymium, praseodymium and mixtures thereof, said composite oxide having a specific surface area of at least 10 m$^2$/g, and being characterized in that it exhibits characteristic peaks corresponding to those of lanthanide-beta -alumina in X-ray diffraction analysis.

2. A process for conducting a catalytic oxidation reaction according to claim 1, wherein the composite oxide has a composition of 1 to 20 molar % of the oxide of at least one member selected from the group consisting of lanthanum, neodymium and praseodymium and the balance being alumina.

3. A process for conducting a catalytic oxidation reaction according to claim 20, wherein the composite oxide has a composition of 3 to 10 molar % of the oxide of at least one member selected from the group consisting of lanthanum, neodymium, and praseodymium and the balance being alumina 4. A process for conducting a catalytic oxidation reaction according to claim 3, wherein the composite oxide has a specific surface area of 20 to 100 m$^2$/g.

5. A process for conducting a catalytic oxidation reaction according to claim 4, wherein the entire support is made of the composite oxide.

6. A process for conducting a catalytic oxidation reaction according to claim 4, wherein the shape of the support is a honeycomb structure.

7. A process for conducting a catalytic oxidation reaction according to claim 4, wherein a surface of a substrate is coated with the composite oxide on which said active component is supported.

8. A process for conducting a catalytic oxidation reaction according to claim 7, wherein the substrate is a member selected from a metallic plate, metallic mesh, and foamed metal.

9. A process for conducting a catalytic oxidation reaction according to claim 4, wherein the active component is at least one member selected from the group consisting of Group VIII elements of the Periodic Table, manganese, chromium, zirconium, rare earth elements, tin, zinc, copper, magnesium, barium, strontium and calcium.

10. A process for conducting a catalystic oxidation reaction according to claim 4, wherein said fluid fuel is methane and said catalytically active component is at least one of the Group VIII elements of Periodic Table.

11. A process for conducting a catalytic oxidation reaction according to claim 6, wherein said active component is at least one Group VIII element of the Periodic Table.

12. A process for conducting a catalytic oxidation reaction according to claim 4, wherein the active component is at least one member selected from the group consisting of Group VIII elements, manganese, chromium, zirconium, rare earth elements, tin, zinc, copper, silver, magnesium, barium, strontium and calcium and the catalyst is contacted with a gas containing the fluid fuel at a temperature of 1500° C. or below to oxidize the fluid fuel.

13. A process according to claim 1, wherein said composite oxide contains less than 1% by weight of chromium, strontium and cerium.

14. A process for conducting a catalytic oxidation reaction, which comprises contacting fluid fuel and an oxidant with a catalyst comprising a support and a catalytically active component supported on said support, wherein at least the part of said support that predominantly supports said active component consists essentially of a composite oxide of alumina and at least one member consisting of the group consisting of lanthanum, neodymium, praseodymium and mixtures thereof, said composite oxide having a specific surface area of at least 10 $m^2/g$, said composite oxide containing less than 1% by weight of chromium, strontium and cerium, and said composite oxide being characterized in that it exhibits characteristic peaks corresponding to those of lanthanide-beta-alumina in the X-ray diffraction analysis and said composite oxide being a calcination product of a mixture of an aluminum compound and a member selected from the group consisting of lanthanum compound, neodymium compound, praseodymium compound and mixtures thereof calcined at a temperature of at least 800° C. for time sufficient to convert the mixture into said composite oxide.

* * * * *